US005545743A

United States Patent [19]

[11] Patent Number: 5,545,743

[45] Date of Patent: Aug. 13, 1996

Cannady et al.

[54] PROCESS FOR HEAT-FRACTIONATION OF ORGANOSILANES

[75] Inventors: John P. Cannady; John M. Gohndrone; Ming-Shin Tzou, all of Midland, Mich.

[73] Assignee: Dow Corning Corporation, Midland, Mich.

[21] Appl. No.: 552,318

[22] Filed: Nov. 2, 1995

[51] Int. Cl.$^{6}$ .......... C07F 7/08

[52] U.S. Cl. .......... 556/466; 203/6

[58] Field of Search .......... 556/466; 203/6

[56] References Cited

U.S. PATENT DOCUMENTS

| | | | |
|---|---|---|---|
| 2,572,302 | 10/1951 | Barry | 260/448.2 |
| 2,594,860 | 4/1952 | Brewer | 260/448.2 |
| 2,626,266 | 1/1953 | Barry | 260/448.2 |
| 2,775,606 | 12/1956 | Wagner et al. | 260/448.2 |
| 4,411,740 | 10/1983 | Flaningam et al. | 556/466 X |
| 5,118,829 | 6/1992 | Gohndrone | 556/481 |
| 5,321,147 | 6/1994 | Chadwick et al. | 556/466 |

OTHER PUBLICATIONS

Wright, J. Organometallic Chemistry 145:307–314 (1978).

*Primary Examiner*—Paul F. Shaver
*Attorney, Agent, or Firm*—William F. Boley

[57] ABSTRACT

An improved process for the heat-fractionation of a mixture comprising an organosilane and a borane or borane forming compound. The improvement comprises the presence of a tertiary organoamine or tertiary phosphorous compound at a concentration sufficient to reduce modification of the organosilane during the heat-fractionation process.

18 Claims, No Drawings

PROCESS FOR HEAT-FRACTIONATION OF ORGANOSILANES

BACKGROUND OF INVENTION

The present invention is an improved process for the heat-fractionation of a mixture comprising an organosilane and a borane or borane forming compound. The improvement comprises the presence of a tertiary organoamine or tertiary phosphorous compound at a concentration sufficient to reduce modifications of the organosilane during the heat-fractionation process.

Methods are known in the art for the production of organosilanes having one or more aryl or cycloalkyl substitutions on the silicon atom. Such processes typically involve the reaction of an aromatic compound or cycloalkane with a silicon hydride in the presence of a Lewis acid as catalyst. The preferred Lewis acid catalyst in such processes is a trihalide boron compound or an organoboron compound. The present inventors believe that in such processes the trihalide boron compound or organoboron compound is reduced to a borane by the silicon hydride to form the active catalytic specie. The present inventors also believe that during conduct of subsequent heat-fractionation processes to isolate the desired organosilanes from the reaction product mixture, borane can act as a redistribution catalyst causing reduced yield of the desired product. Unexpectedly, the present inventors have found that when mixtures comprising an organosilane and a borane or borane forming compound are heat-fractionated in the presence of a tertiary organoamine or tertiary organophosphorus compound redistribution of the reaction product mixture to less commercially desirable compounds can be reduced.

Barry, U.S. Pat. No. 2,572,302, describes a process where a benzenoid hydrocarbon is reacted with an organodichloromonohydrosilane in the presence of boron halide to form aromatic organohalosilanes.

Brewer, U.S. Pat. No. 2,594,860, describes a process where a mixture comprising dichlorosilane and tetrachlorosilane is reacted with benzene in the presence of a boron halide to form phenyltrichlorosilane.

Barry, U.S. Pat. No. 2,626,266, describes a process where a benzenoid hydrocarbon is reacted with trichlorosilane in the presence of a boron halide to form a reaction product where aromatic halosilanes constitute a major portion.

Wagner et al., U.S. Pat. No. 2,775,606, describe a process where a mixture comprising trichlorosilane and dichlorosilane is reacted with benzene to produce a reaction product having as the major component phenyldichlorosilane.

Wright, J. *Organometallic Chemistry* 145:307–314 (1978) describes the reaction of benzene with trichlorosilane in the presence of boron trichloride to form phenyltrichlorosilane. Wright also discusses possible mechanisms for the catalytic activity of the boron trichloride in the process.

Gohndrone, U.S. Pat. No. 5,118,829, describes a process for substituting cycloalkyl substituents for a silicon-bonded hydrogen on a silane. The process employs a preformed organoboron compound as a catalyst.

The described art does not recognize that boranes, particularly in situ formed boranes, can act as a catalyst for detrimental processes in subsequent heat-fractionation steps to isolate preferred organosilane products. Furthermore, the describe art does not recognize that tertiary organoamines and tertiary organophosphorus compounds can reduce modification of organosilanes in mixtures comprising an organosilane and a borane or borane forming compound during a heat-fractionation process.

SUMMARY OF INVENTION

The present invention is an improved process for the heat-fractionation of a mixture comprising an organosilane and a borane or borane forming compound. The improvement comprises the presence of a tertiary organoamine or tertiary phosphorous compound at a concentration sufficient to reduce modification of the organosilane during the heat-fractionation process.

DESCRIPTION OF INVENTION

The present invention is an improved process for heat fractionation of a mixture comprising (A) an organosilane described by formula

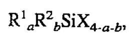

$$R^1_aR^2_bSiX_{4-a-b},$$

where each $R^1$ is independently selected from a group consisting of cycloalkyls comprising 4 to 20 carbon atoms and aryls, each $R^2$ is independently selected from a group consisting of alkyls comprising one to 20 carbon atoms, X is halogen, a=1 or 2, b=0 to 3, and a+b=1 to 4, and (B) a borane or borane forming compound.

The improvement comprises: adding a tertiary amine or tertiary organophosphorus compound at a concentration sufficient to reduce modification of the organosilane during heat fractionation of the mixture.

The present invention is an improved process for heat fractionation of a mixture comprising an organosilane and a borane or borane forming compound. The term "heat fractionation" refers to those processes where heat is applied to the mixture to effect separation of the mixture into two or more fractions, one fraction of which contains the organosilane. The heat fractionation process can be for example a distillation process or a stripping process. The heat fractionation process can be run as a continuous, semi-continuous, or batch process. The heat fractionation can be effected in standard apparatuses suitable for contact with halosilanes.

The mixture which is heat fractionated by the present process comprises an organosilane as described by formula (1). In formula (1) each $R^1$ can be independently selected from a group consisting of aryls and cycloalkyls comprising four to about 20 carbon atoms. $R^1$ can be an aryl such as phenyl, tolyl, and xylyl. $R^1$ can be a cycloalkyl such as cyclopentyl, cyclohexyl, and cycloheptyl. Preferred is when $R^1$ is phenyl. In formula (1), subscript a can be a value of one or two. In formula (1) subscript b can be a value of zero to three, with the preferred value for b being zero or one. The preferred organosilane is selected from a group consisting of methylphenyldichlorosilane and diphenyldichlorosilane.

In addition to the organosilane, the mixture which is heat fractionated by the present process must include a borane or borane forming compound which facilitates rearrangement of the organosilane during the process. The borane can include, for example, $B_{10}H_{14}$, $B_2H_6$, $B_4H_{10}$, $B_5H_9$, $B_5H_{11}$, $B_6H_{10}$, and $H_2C_2B_{10}H_{10}$. The borane may contain alkyl, cycloalkyl, aryl, or silyl groups substituted on the boron atom, for example, compounds such as $B_5H_8(SiCl_3)$, $B_5H_7(SiCl_3)_2$. and $B_5H_8(C_6H_5)$. By borane forming compound it is meant those compounds that can be reduced by a silicon hydride to a borane in situ during the heat fractionation process. The borane forming compound can be, for example, a boron trihalide described by formula $BX^1_3$, where each $X^1$ is an independently selected halogen. The trihalide can be, for example, boron trichloride, boron trifluoride, and boron dichloro bromide. The borane forming compound can be, for example, an organoboron compound such as triphenylboron, phenylboron dichloride, and trimethyl boron, or an organoboron compound such as described by formula

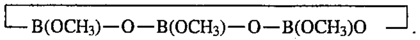

The source of the mixture comprising the organosilane and the borane or borane forming compound is not critical to the present invention. The mixture can be the reaction product resulting from the reaction of a benzenoid hydrocarbon with an organodichloromonohydrosilane in the presence of a boron trihalide as described in, for example, Barry, U.S. Pat. No. 2,572,302. The mixture can be the reaction product resulting from the contact of a cycloalkane with a silicon hydride in the presence of an organoboron catalyst as described, for example, in Gohndrone, U.S. Pat. No. 5,118,829. Other reaction product mixtures which can be separated by the present improved heat fractionation process include, for example, those described in Barry, U.S. Pat. No. 2,626,266; Wagner et al., U.S. Pat. No. 2,775,606; Brewer, U.S. Pat. No. 2,594,860; and Wright, J. of *Organometallic Chemistry* 145:307–314 (1978). A preferred mixture is the reaction product resulting from the reaction of benzene with trichlorosilane, phenyldichlorosilane, or methyldichlorosilane in the presence of boron trichloride. In addition to the desired organosilane i.e. phenyltrichlorosilane, diphenyldichlorosilane, and methylphenyldichlorosilane respectively, the mixture can contain other silanes as well as unreacted feed compounds.

The separation and recovery of organosilane compounds from mixtures by heat-fractionation processes is well known in the art. However the yield of desirable organosilane compounds from such heat-fractionation processes is reduced in the presence of a borane which can act as a catalyst to effect modification of the organosilanes by such processes as redistribution, rearrangement, and degradation at temperatures above about 130° C. The present inventors have found that adding a tertiary organoamine or tertiary organophosphorus compound to the mixture comprising the organosilane and borane or borane forming compound during the heat-fractionation process can reduce the modification of organosilanes present in the mixture. The inventors believe that the tertiary organoamine or tertiary organophosphorus compound forms a stable complex with borane thereby reducing the ability of borane to act as a catalyst to effect the modification of the organosilanes. Therefore, any tertiary amine or tertiary organophosphorus compound capable of forming a stable complex with the borane under the heat-fractionation process conditions may be used in the present process.

The tertiary organoamine can be, for example, described by formula $R^3{}_3N$, where each $R^3$ is an independently selected hydrocarbon radical comprising one to 20 carbon atoms. $R^3$ can be, for example, an alkyl such as methyl, ethyl, t-butyl, octyl, and dodecyl; an aryl such as phenyl and tolyl; or a aralkyl such as benzyl and beta-phenylethyl. The tertiary organoamine can be, for example, a diamine such as N,N,N',N'-tetramethylethylenediamine. The tertiary organoamine can be a higher organoamine described by, for example, formula $R^3{}_2N\{(CH_2)_xNR^3\}_y(CH_2)_xNR^3{}_2$; where $R^3$ is as previously described, subscript x is one to about 20, and subscript y is one to about 20. Preferred is when x is 2 and y is one.

The tertiary organoamine can be, for example, triphenylamine, tribenzylamine, triethylamine, trimethylamine, trioctylamine, and tridodecylamine. Preferred is when the tertiary organoamine has a $pK_a$ value greater than about 10. Even more preferred is when the tertiary organoamine as a $pK_a$ value greater than about 11. It is preferred that the tertiary organoamine have a boiling point temperature greater than that of the organosilane, to reduce carry-over during the heat-fractionation process. When the major organosilane compound in the mixture is methylphenyldichlorosilane the preferred tertiary organoamine is trioctylamine. When the major organosilane compound in the mixture is diphenyldichlorosilane the preferred tertiary organoamine is tridodecylamine.

Tertiary organophosphorus compounds useful in the present process are, in general, of the same type as described for the tertiary organoamine, where the phosphorous atom is substituted for the nitrogen atom in the compound. The tertiary organophosphorus compound can be, for example, of formula $R^3{}_3P$, where $R^3$ is as previously described. The tertiary organophosphorus compound can be a compound containing more than one phosphorous atom such as 1,2-bis(diphenylphosphino)ethane. It is preferred that the tertiary organophosphorus compound have a boiling point temperature greater than that of the organosilane to reduce carry-over during the heat-fractionation process.

The tertiary organoamine or tertiary organophosphorus compound is added to the heat-fractionation process at a concentration sufficient to reduce modification of the organosilane during conduct of the process. The useful concentration of tertiary organoamine or tertiary organophosphorus compound will depend upon such factors as the chemical composition of the tertiary organoamine and tertiary organophosphorus compounds and the type and concentration of borane present in the mixture. In general, adding the tertiary organoamine or tertiary organophosphorus compound to provide a nitrogen to boron (N/B) mole ratio or phosphorous to boron (P/B) mole ratio of about 0.1 to 10 is considered useful. More preferred is when the tertiary organoamine or tertiary organophosphorus compound is added at a concentration providing a N/B mole ratio or P/B mole ratio within a range of about 0.1 to five. Most preferred is when tertiary organoamine or tertiary organophosphorus compound is added at a concentration providing a N/B mole ratio or P/B mole ratio of about one.

The following examples are provided to illustrate the present invention. The examples are not intended to limit the claims herein.

EXAMPLE 1

A crude product mixture containing diphenyldichlorosilane was prepared by heating at a temperature of 250° C. and a pressure of 8.3 MPa a mixture comprising dichlorosilane, trichlorosilane, and benzene in the presence of boron trichloride as catalyst. About 83.3 g of the crude product mixture containing 32 g of diphenyldichlorosilane was placed in a flask. The mixture was stripped at 1 atm of pressure and up to a temperature of 300° C. The volatiles were condensed and analyzed by gas chromatography using a thermal conductivity detector (GC-TCD). The collected liquid comprised 10.8 g of diphenyldichlorosilane (Yield of 32 percent, where yield is based upon the weight recovery of diphenyldichlorosilane present in the crude product mixture.), 3.4 g of phenyldichlorosilane, 37.8 g of phenyltrichlorosilane, and 13.8 g of benzene.

EXAMPLE 2

Triethylamine (3.9 g) was added to a flask containing 83.3 g of the crude product mixture described in Example 1. This mixture was stripped by the process described in Example 1. The volatiles were condensed and analyzed by GC-TCD. About 77.4 g of a liquid was recovered comprising 24.7 g of diphenyldichlorosilane (yield of 77 percent), 1.4 g of phenyldichlorosilane, 24.5 g of phenyltrichlorosilane, and 10.1 g of benzene.

EXAMPLE 3

About 6.3 g of $Ph_2PCH_2CH_2PPh_2$ was placed in a flask containing 128 g of the crude product mixture described in Example 1. This mixture was stripped at 1 atm. of pressure and up to a temperature of 330° C. The volatiles were condensed and analyzed by GC-TCD. The collected liquid comprised 36 g of diphenyldichlorosilane (yield of 80 percent) and 33.7 g of phenyltrichlorosilane.

EXAMPLE 4

About 225 g of a crude product mixture prepared by the process described in Example 1 and containing 94 g of diphenyldichlorosilane was added into a flask equipped with a distillation head, a 30 cm distillation column, and a thermometer. Eight grams of triphenylamine were added to the flask. This mixture was distilled at 70 mm Hg pressure up to a temperature of 270° C. When the temperature reached 200° C., 111 g of liquid had been collected from the column. The collected liquid was analyzed by GC-TCD. This liquid fraction comprised 3 g of diphenyldichlorosilane, 80 g of phenyltrichlorosilane and 21 g of benzene. The total liquid collected from the column between the temperatures of 200° C. and 210° C. was 85 g, of which diphenyldichlorosilane was 83 g. Distillation was continued up to a temperature of 270° C. The total recovery of diphenyldichlorosilane was 92 percent.

EXAMPLE 5

The process described in Example 4 was repeated in the absence of the triphenylamine. A total of 62 g of diphenyldichlorosilane was recovered, as determined by GC-TCD (yield of 66 percent).

EXAMPLE 6

About 228 g of the crude product mixture described in Example 4 and containing 10 g of triphenylamine was distilled at a pressure of 20 mm Hg. The distillation apparatus was the same as described in example 4. Initially, the mixture was heated to 200° C. to remove benzene. The distillation apparatus was then evacuated to 20 mm Hg and distillation continued until the solution temperature of the flask reached 250° C. The liquid collected at a temperature less this 160° C. comprised 1.3 g of diphenyldichlorosilane, 3.3 g phenyldichlorosilane, and 71.4 g phenyltrichlorosilane, as determined by GC-TCD. The liquid collected at a temperature between 160° C. and 187° C. comprised 89 g of diphenyldichlorosilane and 1 g of phenyltrichlorosilane. The yield of diphenyldichlorosilane was 96 percent.

EXAMPLE 7

The process described in Example 6 was repeated in the absence of the triphenylamine. About 76 g of diphenyldichlorosilane was recovered, as determined by GC-TCD (yield of 81 percent).

EXAMPLE 8

A crude product mixture comprising methylphenyldichlorosilane was prepared by contacting a reaction mixture comprising methyldichlorosilane and benzene in the presence of boron trichloride catalyst at a temperature of 270° C. and a pressure of 8.3 MPa. About 1600 g of a crude product mixture containing 17 GC-TCD area percent methylphenyldichlorosilane was placed in a flask equipped with a thermometer and a 10 tray bubble-cap distillation column. Then, 52 g of distilled tri-n-octylamine was added to the flask. The content of the flask was heated at a temperature below 210° C. to remove low boilers comprising primarily methyldichlorosilane and benzene. The temperature of the flask was then heated to 210° C. and kept at this temperature for 48 hours. The content of the flask was distilled at a pressure of 20 mm Hg and a distillation head temperature of about 104° C. About 240 g of methylphenyldichlorosilane (99.3 GC-TCD area percent) was collected (yield of 88%), having a purity of 99%+ and nitrogen content of 10 ppm.

EXAMPLE 9

The process described in Example 8 was repeated in the absence of the tri-n-octylamine. After the low boilers were removed by distillation, the solution was heated at 160° C. for 24 hours. The resulting mixture was analyzed by GC-TCD and found to contain only about five percent by weight of methylphenyldichlorosilane.

EXAMPLE 10

About 18.8 g of tridodecylamine was placed in a flask containing 352 g of the crude product mixture described in Example 1. The mixture was heated up to a temperature of 210° C. for 48 hours to remove low-boilers. Phenyltrichlorosilane was removed by distillation at a temperature of 100° C. and 20 mm Hg. The residual solution was heated at 210° C. for another 48 hours. Diphenyldichlorosilane was recovered by distillation at a temperature of 185° C. and 20 mm Hg, and the yield determined by GC-TCD to be 80 percent.

EXAMPLE 11

About 7.22 g of N,N,N',N'-tetramethylethylenediamine was placed in a flask containing 436 g of the crude product mixture described in Example 1. The mixture was heated up to a temperature of 210° C. for 48 hours to remove low-boilers. Phenyltrichlorosilane was removed by distillation at a temperature of 100° C. at 20 mm Hg. The residual solution was heated at 210° C. for another 96 hours. Diphenyldichlorosilane was recovered by distillation at a temperature of 190° C. and 20 mm Hg, and the yield determined by GC-TCD to-be 70 percent.

EXAMPLE 12

About 4.45 g of pentethylenehexamine was placed in a flask containing 495 g of the crude product mixture described in Example 1. The mixture was heated up to a temperature of 210° C. for 48 hours to remove low-boilers. Phenyltrichlorosilane was removed by distillation at a temperature of 100° C. and 20 mm Hg. The residual solution was heated at 210° C. for another 96 hours. Diphenyldichlorosilane was recovered by distillation at a temperature of 185° C. and 20 mm Hg, and the yield determined by GC-TCD to be 70 percent.

EXAMPLE 13

About 11 g of 1,2-bis(diphenylphosphino)ethane was placed in a flask containing 495 g of the crude product mixture described in Example 1. The mixture was heated up to a temperature of 210° C. for 48 hours to remove low-boilers. Phenyltrichlorosilane was removed by distillation at a temperature of 100° C. and 20 mm Hg. The residual solution was heated at 210° C. for another 96 hours. Diphenyldichlorosilane was recovered by distillation at a temperature of 190° C. and 20 mm Hg, and the yield determined by GC-TCD to be 60 percent.

We claim:

1. In a process for heat fractionation of a mixture comprising (A) an organosilane described by formula $$R^1_aR^2_bSiX_{4-a-b},$$

where each $R^1$ is independently selected from a group consisting of cycloalkyls comprising 4 to 20 carbon atoms and aryls, each $R^2$ is independently selected from a group consisting of alkyls comprising one to 20 carbon atoms, X is halogen, a=1 or 2, b=0 to 3, and a+b=1 to 4, and (B) a borane or borane forming compound; the improvement comprising: adding a tertiary amine or tertiary organophosphorus compound at a concentration sufficient to reduce modification of the organosilane during heat fractionation of the mixture.

2. A process according to claim 1, where the organosilane is selected from a group consisting of methylphenyldichlorosilane and diphenyldichlorosilane.

3. A process according to claim 1, where the borane is selected from a group consisting of $B_{10}H_{14}$, $B_2H_6$, $B_4H_{10}$, $B_5H_9$, $B_5H_{11}$, $B_6H_{10}$, $B_5H_8(SiCl_3)$, $B_5H_7(SiCl_3)_2$, $B_5H_8(C_6H_5)$, and $H_2C_2B_{10}H_{10}$.

4. A process according to claim 1, where the borane forming compound is boron trichloride.

5. A process according to claim 1, where the borane forming compound is an organoboron.

6. A process according to claim 1, where the borane forming compound is triphenylboron.

7. A process according to claim 1, where the mixture comprising the organosilane and the borane or borane forming compound results from the reaction of benzene with a chlorosilane selected from a group consisting of trichlorosilane, phenyldichlorosilane, and methyldichlorosilane in the presence of boron trichloride.

8. A process according to claim 1, where the tertiary organoamine is described by formula $R^3{}_3N$, where each $R^3$ is an independently selected hydrocarbon radical comprising one to 20 carbon atoms.

9. A process according to claim 1, where the tertiary organoamine is selected from a group consisting of triphenylamine, tribenzylamine, triethylamine, trimethylamine, trioctylamine, and tridodecylamine.

10. A process according to claim 1, where the tertiary organoamine is N,N,N',N'-tetramethylethylenediamine.

11. A process according to claim 1, where the tertiary organoamine has a $pK_a$ value greater than about 10.

12. A process according to claim 1, where the tertiary organoamine has a $pK_a$ value greater than about 11.

13. A process according to claim 1, where the organosilane is methylphenyldichlorosilane and the tertiary organoamine is trioctylamine.

14. A process according to claim 1, where the organosilane is diphenyldichlorosilane and the tertiary organoamine is tridodecylamine.

15. A process according to claim 1, where the tertiary organophosphorus compound is 1,2-bis(diphenylphosphino-)ethane.

16. A process according to claim 1, where the tertiary organoamine or tertiary organophosphorus compound is added to the process in an amount sufficient to provide a nitrogen to boron mole ratio or phosphorous to boron mole ratio of about 0.1 to 10.

17. A process according to claim 1, where the tertiary organoamine or tertiary organophosphorus compound is added to the process in an amount sufficient to provide a nitrogen to boron mole ratio or phosphorous to boron mole ratio within a range of about 0.1 to five.

18. A process according to claim 1, where the tertiary organoamine or tertiary organophosphorus compound is added to the process in an amount sufficient to provide a nitrogen to boron mole ratio or phosphorous to boron mole ratio of about one.

* * * * *